United States Patent [19]

Cotti

[11] 3,962,331
[45] June 8, 1976

[54] PROCESS FOR THE PREPARATION OF α-6-DEOXYTETRACYCLINES

[75] Inventor: Gino Cotti, Monza, Italy

[73] Assignee: Ankerfarm, S.p.A., Milan, Italy

[22] Filed: Sept. 25, 1974

[21] Appl. No.: 509,055

[30] Foreign Application Priority Data
Sept. 28, 1973 Italy.................................. 29487/73

[52] U.S. Cl........................................... 260/559 AT
[51] Int. Cl.$^2$........................................ C07C 103/22
[58] Field of Search............................... 260/559 AT

[56] References Cited
UNITED STATES PATENTS

| | | | |
|---|---|---|---|
| 3,250,809 | 5/1966 | Blackwood et al........... | 260/559 AT |
| 3,649,700 | 3/1972 | Baader et al.................. | 260/654 D |
| 3,659,006 | 4/1972 | Pande........................... | 260/465.7 |

OTHER PUBLICATIONS
Borowitz et al., JACS, 94:19, 9-20-72; 6817–6822.

Primary Examiner—C. Davis
Attorney, Agent, or Firm—Stevens, Davis, Miller & Mosher

[57] ABSTRACT

This invention relates to a process for the preparation of α-6-deoxytetracyclines, by the simultaneous reductive dehalogenation and reduction by hydrogen, in a polar solvent of the corresponding 11a-halo-6-demethyl-6-deoxy-6-methylene-tetracycline, in presence of a suitable member of the group of the tertiary phosphines, arsines and stibines, as regards the dehalogenation and of a catalyst, selected from amongst the complexes of noble metals with electron-donor ligands, soluble in the reaction medium, whereby the reaction is carried out according to the mechanism of the homogeneous catalysis.

5 Claims, No Drawings

PROCESS FOR THE PREPARATION OF α-6-DEOXYTETRACYCLINES

The present invention concerns a process for the preparation of α-6-deoxytetracyclines by means of reductive dehalogenation and hydrogenation of the corresponding 11a-halo-6-demethyl-6-deoxy-6-methylene-tetracyclines.

More exactly, the process according to the invention makes it possible to achieve simultaneously, in one step only, the reductive dehalogenation to 6-demethyl-6-deoxy-6-methylene-tetracyclines, obtained with suitable use of tertiary phosphines, arsines of stibines, and subsequent hydrogenation to 6-deoxy-tetracyclines according to a mode of action of homogeneous catalysis, based on the use of catalysts soluble in the reaction means.

In a suitable polar solvent, starting from compounds of the type I

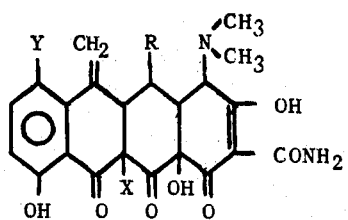

in which:
X = halogen
R = —H, —OH, —O—COR' (R' = alkyl group containing from 1 to 6 carbon atoms)
Y = —H, halogen or from their salts with the mineral or organic acids, or from their complexes with the salts of polyvalent metals, there are obtained the α isomers of the corresponding 6-deoxytetracyclines of the type III

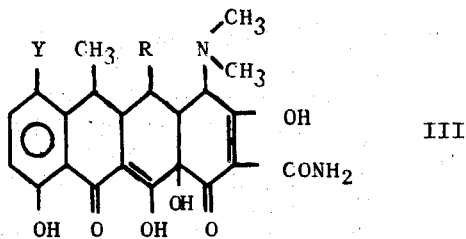

where Y, R and R' have the same meaning as stated above.

The 6-deoxytetracyclines are known antibiotics; the U.S. Pat. Nos. 3,019,260 and 3,200,149, the SA Pat. No. 674,307, the British Pat. No. 845,649, the French Pat. No. 1,238,750, the Belgian Pat. No. 565,025 describe their preparation with the use of variously supported noble metals.

There is also known the use of heterogeneous, partially poisoned catalysts described in the French Pat. No. 1,557,970, which favour prevalence of the α-isomers over the β-isomers. In particular, the Applicant has filed the German patent application No. P 23 08 227.1 relating to a method of preparation of α-6-deoxytetracyclines by means of homogeneous catalytic hydrogenation of the corresponding 6-demethyl-6-deoxy-6-methylene tetracyclines; suitable catalysts are coordination compounds of noble metals with electron-donor ligands; the compounds in question can be prepared in situ by placing into contact suitable amounts of ligand and noble metal halide.

The applicant has also filed another patent application concerning a process for the preparation of 6-demethyl-6-deoxy-6-methylene tetracycline by means of reductive dehalogenation caused by placing into contact, in appropriate conditions and in a polar solvent, an 11a-halo-6-demethyl-6-deoxy-6-methylene-tetracycline with a tertiary phosphine, stibine or arsine.

The applicant has now found that the two processes

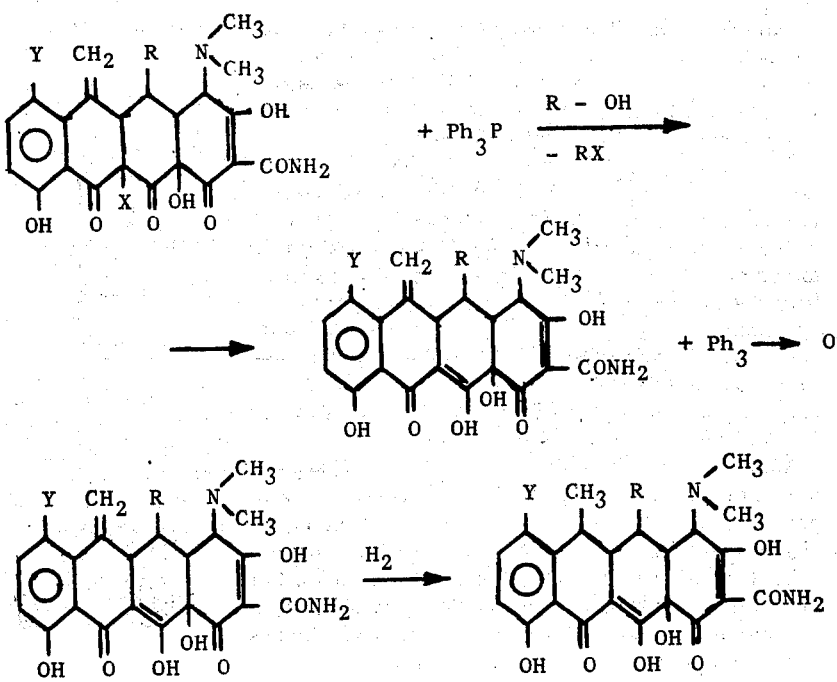

can be carried out simultaneously, in a single step, using suitable amounts of reagents.

More exactly, the process according to the invention is realized by placing a compound of the tetracycline group having the general formula I together with a stoichiometric quantity of a tertiary arsine, phosphine or stibine and a catalytic quantity of a homogeneous hydrogenation catalyst consisting of a noble metal coordination compound with electron-donor ligands, into contact with hydrogen in a suitable solvent, at a temperature and at a pressure and for a period of time sufficient to obtain a complete conversion.

The hydrogenation leads, in selective manner, to the formation of α-isomers.

The catalyst may be formed in situ; in such case there will be introduced a noble metal halide together with a number of moles of ligand per mole of metal greater than 1.

Particularly indicated are triphenylphosphine and the complexes of rhodium with triphenylphosphine of the type RhCl (Ph$_3$P)$_3$, the dimer Rh$_2$Cl$_2$(Ph$_3$P)$_4$, the hydride and dihydride derivatives RhHCl$_2$(Ph$_3$P)$_3$, Rh H$_2$Cl (Ph$_3$P)$_3$ and the complex Rh (Ph$_3$P)$_3$ Cl$_3$; the mode of action of the hydrogenation is described in the German patent application No. P 23 08 227.1 filed by the applicant.

According to the process of the present invention, a compound of the group of the tetracyclines having general formula I, a stoichiometric quantity of triphenylphosphine and a catalytic quantity of a complex, of the previously indicated type, are dissolved in a suitable solvent and placed into contact with hydrogen in conditions such as will permit total conversion into hydrogenated compound.

From the clear solution found at the end of the reaction there are separated, with very high yields, the α-6-deoxy-tetracyclines of the general formula III, while the homogeneous catalyst and the oxide of triphenylphosphine remain in solution in the mother liquors.

Suitable solvents are mono- or poly-hydroxylated alcohols having from 1 to 4 carbon atoms, methoxyethanol, ethoxyethanol and their mixtures with acetonitrile, tetrahydrofuran, dioxane, acetone, N,N' dimethyl-formamide and methylisobutylketone.

The speed of reaction depends above all on the temperature: at temperatures lower than 10°C the reaction is excessively slow, at temperatures higher than 100°C degradation products form. The best results are obtained between 40°C and 80°C. The pressure can vary from 1 to 160 kg/cm². The triphenylphosphine should be added in the ratio of one mole per mole of tetracycline; should it be wished to prepare the catalyst in situ, to the amount necessary for the dehalogenation it is necessary to add triphenyl-phosphine in the measure of 1–4 moles per mole of noble metal halide.

Amounts of ligand lower than 1 lead to the separation of metal which acts as heterogeneous catalyst with prevalent formation of β-epimer. Amounts of ligand higher than 4 lead to homogeneous catalysts with gradually decreasing yields and incomplete conversions of the substrate, while the stereospecificity remains high.

There are now given some non-restrictive Examples of the execution of the present invention.

EXAMPLE I 13.6 g of 11a-chloro-6-demethyl-6-deoxy-6-methylene-5-oxytetracycline p-toluenesulfonate, 0.125 g of RhCl$_3$.3H$_2$O and 5.85 g of Ph$_3$P were dissolved in 100 ml of MeOH in an atmosphere of inert gas.

The solution was transferred into an autoclave and hydrogenated for 2 hours at 80°C and at 30 kg/cm².

At the end of the said period there was obtained a clear solution, of a light yellow colour which, on contact with air, darkens rapidly.

Thin layer chromatography (using chromatoplates covered with Kieselguhr and buffered to pH 9, eluant H$_2$O-Me$_2$CO (10:1), U.V. light as detector) performed on the crude reaction product gave the following result: α-6-doxycycline: approximately 95%; β-6-doxycycline: approximately 5%; slight traces of degradation products.

Using conventional methods, isolation was made of 6.8 g of α-6doxycycline base giving a spectrophotometric assay of 98.9%.

EXAMPLE II

To 27.2 g of 11a-chloro-6-demethyl-6-deoxy-6-methylene-5-oxytetracycline p-toluenesulfonate addition was made of 0.48 g of tris-(triphenylphosphine)-rhodium (I) chloride and 5.486 g of Ph$_3$P in 200 ml of MeOH. Hydrogenation was carried out at 20 kg/cm² and at 80°C for 2 hours.

From the clear solution found at the end of the reaction, after removal of the catalyst by crystallization, conventional methods were used to isolate 13.4 g of α-6-doxycycline base giving a spectrophotometric assay of 99.3%.

EXAMPLE III 39.9 g of 11a-fluoro-6-demethyl-6-deoxy-5-oxytetracycline p-toluenesulfonate were dissolved in 1000 ml of dimethylacetamide and 100 ml of MeOH with 8.229 g of Ph$_3$P and 0.74 g of RhCl (Ph$_3$P)$_3$: hydrogenation was carried out for 3 hours at 60°C and at 60 kg/cm² and produced a clear solution which subsequent TLC revealed as having a complete conversion and a α/β epimer ratio of 18:1.

EXAMPLE IV 14.5 g of 11a-bromo-6-demethyl-6-deoxy-6-methylene-5-oxytetracycline p-toluenesulfonate was treated with 0.25 g of RhCl$_3$ 3H$_2$O and 6.625 g of Ph$_3$P in 100 ml of MeOH.

After 4 hours of hydrogenation at 60°C and at 35 kg/cm², addition was made of 10 g of sulfosalicyclic acid; there was crystallization of 11 g of α-6-doxycycline sulfosalicylate from which was obtained 6.55 g of α-6-doxycycline base having a high degree of purity.

EXAMPLE V 3.58 g of 11a-chloro-6-demethyl-6-deoxy-6-methylene-5-acetoxytetracycline mesylate was dissolved in N,N'-dimethylformamide-MeOH and hydrogenated as described in the Example 1, there being obtained an almost complete conversion into α-6-deoxy-6-demethyl-6-methylene-5-acetoxytetracycline.

What I claim is:

1. A process for the preparation of α-6-deoxytetracycline having the general formula III

[Structure III shown: tetracycline skeleton with substituents Y, CH₃, R, N(CH₃)₂, OH, CONH₂, OH, O, OH, O]

where
R = H, —OH, —O—CO—R' (—R' = alkyl group containing from 1 to 6 C atoms)
Y = H - halogen by means of the dehalogenation and homogeneous catalytic hydrogenation of 11a-halo-6-demethyl-6-deoxy-6-methylene tetracyclines having the general formula I

[Structure I shown: tetracycline skeleton with Y, CH₂, R, N(CH₃)₂, OH, CONH₂, OH, X, O, OH, O]

effected in a single step without isolating intermediate products of general formula II

[Structure II shown: tetracycline skeleton with Y, CH₂, R, N(CH₃)₂, OH, CONH₂, OH, O, OH, O]

where
Y, R have the meaning stated heretofore
X = halogen
with the use respectively of tertiary phosphines, arsines and stibines in the measure of one mole per mole of tetracycline group compound, of catalysts soluble in the reaction means consisting of complexes of noble metals with electron-donor ligands of the type of the tertiary phosphines, arsines, stibines, in a reaction solvent selected from the group consisting of alcohols containing at least one hydroxy group and from 1 to 4 C atoms, methoxyethanol, ethoxyethanol and their mixtures and said alcohols and their mixtures with at least one of acetonitrile, tetrahydrofuran, dioxane, acetone, N,N'-dimethylformamide and methylisobutylketone at temperatures comprised between 10°C and 100°C, for periods of time of from 1 to 8 hours in the presence of hydrogen and at pressures of from 1 to 160 kg/cm$^2$.

2. A process according to claim 1, characterized by the fact that the reductive dehalogenation is obtained with triphenylphosphine and that the homogeneous catalyst is a complex of rhodium with triphenylphosphine and more exactly RhCl (Ph$_3$P)$_3$ or RhCl (Ph$_3$P)$_2$, the dimer Rh$_2$Cl$_2$ (Ph$_3$P)$_4$, the hydride derivative RhHCl$_2$ (Ph$_3$P)$_3$, the dihydride derivative RhH$_2$Cl (Ph$_3$P)$_3$ or one of the solvates obtained from the aforesaid complexes in solution of the solvents specified in the claim 1.

3. A process according to claim 2, characterized by the fact that the soluble catalyst RhCl(Ph$_3$P)$_3$, or its derivatives as specified in the claim 2, are prepared directly in the reaction means by reacting RhCl$_3$-3H$_2$O with triphenylphosphine employed in an amount necessary for the reductive dehalogenation.

4. The process according to claim 1 wherein said temperature is between 60°C and 80°C.

5. The process according to claim 1 wherein said pressure is between 30 and 50 kg/cm$^2$.

* * * * *